United States Patent [19]

Nochumson et al.

[11] 4,415,428

[45] Nov. 15, 1983

[54] SUPPORT FOR ELECTROPHORESIS AND METHOD OF PRODUCING SAME

[75] Inventors: Samuel Nochumson, Rockland; Henry J. Witt, Rockport, both of Me.

[73] Assignee: FMC Corporation, Philadelphia, Pa.

[21] Appl. No.: 342,993

[22] Filed: Jan. 27, 1982

[51] Int. Cl.$^3$ ................................................ B01K 5/00
[52] U.S. Cl. ........................... 204/299 R; 204/180 G; 204/180 S; 204/301
[58] Field of Search ............ 204/180 G, 180 S, 299 R, 204/301

[56] References Cited

U.S. PATENT DOCUMENTS 4,319,975  3/1982  Cook ............................... 204/299 R

*Primary Examiner*—Winston A. Douglas
*Assistant Examiner*—B. J. Boggs, Jr.
*Attorney, Agent, or Firm*—Robert D. Jackson; Eugene G. Horsky; Eugene G. Seems

[57] ABSTRACT

An electrophoretic support comprising a base plate having on at least one side thereof, a layer of an adherent resin containing ethylenically unsaturated groups capable of undergoing copolymerization with acrylamide. The support provides excellent adhesion for polyacrylamide gels and other electrophoretic media such as agarose.

16 Claims, No Drawings

SUPPORT FOR ELECTROPHORESIS AND METHOD OF PRODUCING SAME

This invention relates to electrophoresis and in particular to a support for electrophoretic gel films and a method of producing and using it in thin film electrophoretic processes.

Electrophoresis is a well-known technique for the separation of charged species by utilizing their differences in rate of migration under the influence of an electrical field. The procedure has proved invaluable for the resolution and isolation of complex biological substances such as enzymes, serums, carbohydrates, proteins, including albumin and globulins and the like. Most analytical electrophoresis methods are based on zone electrophoresis in which a thin zone of the sample is applied to the electrophoretic medium. The electrophoretic migration of the sample components results in the formation of fractional zones which can then be examined and studied by application of standard electrophoretic practices such as fixing, staining and washing to remove buffers. Desirably, the electrophoretic media is a thin gel film coated on a suitable support, commonly glass or plastic. Such an arrangement permits the electrophoretic separation to be achieved in a minimum of time with a maximum degree of resolution.

Various hydrophilic colloids, for example, starch, agarose, and cellulose derivatives have been used in forming electrophoretic gel films, but polyacrylamide is much favored. One reason for choosing polyacrylamide is that gels can be prepared from it having a wide range of pore sizes. This is accomplished primarily by varying the ratio of acrylamide monomer to the N,N'-methylenebisacrylamide cross-linking reagent.

The resulting polyacrylamide gels provide high resolution electrophoretic separations of important biopolymers, for example, proteins and nucleic acids. In addition, the absence of ionized groups in polyacrylamide gels render them suitable as an anticonvection medium for isoelectric focusing.

In isoelectric focusing, with which the present invention is also concerned, a pH gradient is established across an electric potential, and ampholytes such as proteins and the like are separated and fractionated in this pH gradient. Since the proteins or other charged entities are concentrated at the position of the isoelectric pH point, the fractionation is sharp and clean. Thus, in regard to resolving power, isoelectric focusing exceeds that of other electrophoretic processes. Moreover, the isoelectric end point is much easier to determine in isoelectric focusing than with conventional electrophoretic procedures. Another advantages of isoelectric focusing is that the zones of fractionated proteins do not move from the position of the isoelectric point and therefore the sharpness of the separated zone is free from degradation caused by diffusion.

In carrying out zone electrophoresis such as thin layer isoelectric focusing, a suitable support is required to prevent the gel layer from fracturing, especially during such manipulations involving fixing, staining and destaining in order to visualize the protein separation pattern. Generally, a support for thin layer isoelectric focusing should include the following characteristics: (1) Dimensional stability; (2) Thermal stability; (3) Transparency; (4) Heat conductivity; (5) Abrasion resistance and (6) Gel retention.

One approach to providing a support for polyacrylamide isoelectric focusing is described in "Proceedings of the Second International Conference on Electrophoresis", Munich, Germany Oct. 15–17, 1979 and published by Walter de Gruyter, Berlin, New York, 1980, as "Electrophoresis '79", B. J. Radola, editor. This support consists of a base plate at least one side of which has applied thereto a coating of methacryloxypropyl-trimethoxy-silane of the formula:

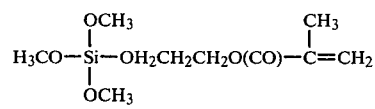

A polyacrylamide gel layer is then formed on the coated side of the support in the conventional manner by placing in contact therewith a polymerizable mixture of acrylamide and N,N-methylenebisacrylamide and effecting polymerization of the mixture. During the polymerization, residual unsaturated groups in the methacrylate silane cross-link with those in the acrylamide mixture thereby effecting covalent bonding of the gel layer with the silanized coating.

According to the Radola publication, of a variety of supports tested, those prepared from glass plates and polyester films, as a base plate for the silanized coatings, proved to be the best. Polyester film has the advantage over glass of being flexible for easier handling and storing in addition to exhibiting the other desirable support features previously enunciated elsewhere herein. The surface of such base plates is described as containing reactive sites which chemically bond with the silicon functional groups in the silane compounds. In the case of a glass base plate, —OH groups on the glass surface are capable of reacting with one or more of the —OCH$_3$ groups to eliminate CH$_3$OH with formation of Si-O bonds. In the case of polyester film base plates, however, the plastic material thereof is too chemically inert to combine with the organosilicon compound. Therefore, Radola subjects the polyester film to an activation pretreatment with sodium hydroxide solution which cleaves some of the ester bonds resulting in the formation of functional groups, presumably free —OH radicals, on the film surface thereby affording reactive sites for chemical attachment of the silane. In effect, the initially hydrophobic surface of the polyester film is rendered hydrophilic to a certain degree by the sodium hydroxide, depending on the extent of the ester cleavage.

However, electrophoretic supports prepared from polyester film by this procedure are not satisfactory. This is not too surprising considering the dilemma presented of providing adequate adhesion of the reactive silane coating while maintaining film transparency. Thus, if given sufficient alkaline pretreatment to ensure adhesion of the coating, the polyester film becomes cloudy or even opaque; on the other hand, less vigorous alkaline treatment preserves film transparency but adhesion of the coating suffers. Even where there is strong bonding between the silane layer and base plate, whether glass or modified film, adhesion problems of a different sort can occur. Such problems arise when the acid sensitive ester functions in the silane coating compositions of Radola undergo hydrolytic cleavage forming free acrylic acid and OH moieties. This can result in the gel film becoming detached during electrophoresis or in processing the separation zones, that is, fixing, staining and destaining under acidic conditions.

Moreover, other electrophoretic gel media, such as agarose which have no ethylenic unsaturation, exhibit rather poor affinity for the supports of Radola. Apparently, where no opportunity is presented for covalent bonding, as with polyacrylamide gels, the merely physical forces of attraction between the silanized surfaces of Radola and the electrophoretic medium afford inadequate adhesion.

It is, accordingly, a primary object of the present invention to provide an electrophoretic support having improved adhesion for electrophoretic gel films and a method of producing and using it.

It is a more particular object of the invention to provide a flexible electrophoretic support having improved adhesion for polyacrylamide and agarose gel films and a method of producing and using it.

Other objects and purposes will be made manifest subsequently herein.

The objects aforesaid are realized by establishing on at least one side of a suitable base plate, a layer of an adherent resin containing reactive ethylenically unsaturated groups by which is understood the groups are capable of undergoing copolymerization with an acrylamide/N,N-methylenebisacrylamide polymerizable mixture when placed in contact with said resin surface. Such a layer can be established by applying to the base plate a coating of a resin composition containing the ethylenically unsaturated groups and which is capable of adhering to the base plate and not be damaged or become detached during the electrophoretic operation. The base plate may, depending on its composition, require a pretreatment or the application of a priming layer to insure satisfactory attachment of the resin coating. Such techniques, some of which are described in detail elsewhere herein, are generally well-known.

Adhesion of the resin to the base plate can involve physical and/or chemical forces. For example, physical bonding of the coating to the support can usually be accomplished by matching the polar character of the base plate on the one hand and that of the resin coating on the other. Thus, a hydrophobic support media will tend to bind a hydrophobic resin more firmly than a hydrophilic type and vice versa. Where the support plate surface and resin contain chemical functions which can mutually interact, the resin will be bound to the substrate via chemical forces. For instance, chemical bonding can be effected by incorporating ester or acid groups in a polymeric film capable of reacting with amino groups in the resin thereby forming amide linkages across the support plate and resin layer; ether or ester linkages can also be utilized to promote chemical bonding.

The electrophoretic supports of the invention are capable of adhering electrophoretic gel media of the type commonly employed in thin film electrophoresis. Where the electrophoretic gel is polyacrylamide, excellent adhesion to the herein supports is attained by virtue of the copolymerization between the ethylenically unsaturated group in the resin layer and those in the polymerizing mixture of acrylamide/N,N-methylenebisacrylamide monomers during casting of the polyacrylamide gel on the support. The gel is thus firmly attached by covalent linkages to the resin layer; even ultra thin polyacrylamide coatings, highly desired for electrofocusing, are tightly held. Where there is no opportunity presented for chemical interaction between the gel and the resin layer, such as the copolymerization aforesaid, then adhesion by physical forces must be relied on, for example, hydrogen bonding and/or Van der Vaal forces. Thus, hydrophilic gels such as agarose can be made to adhere to the electrophoretic supports of the invention provided the resin layer to which the gel is applied is itself hydrophilic in character. The degree of hydrophilic properties can be controlled by selecting a resin composition which is complementary in polarity to that of the electrophoretic gel. However, such matching of polarity is not critical in the case of polyacrylamide since the gel is attached to the resin layer by chemical bonding. In fact, polyacrylamide gel, although a hydrophilic colloid, can be made to adhere quite strongly to a hydrophobic resin layer through covalent bonding with the ethylenically unsaturated groups in the resin.

Suitable examples of a base plate for receiving the resin layers or coatings herein include films made from such organoplastic materials as polystyrene, polypropylene, styreneacrylonitrile copolymers, polycarbonate, cellulose acetate propionate, cellulose acetate butyrate, nitrile-acrylonitrilestyrene copolymers, polyacrylate, polyterephthalate, polymethacrylate, acrylonitrile-butadiene-styrene copolymers and the like. Preferably, the film base is a polyester type, most preferably a polyterephthalate.

The hydrophilic resins used in producing the coatings for the electrophoretic supports of the invention are conveniently obtained by replacing at least one of the active hydrogens in a hydrophilic, film-forming resin with a substituent having ethylenically unsaturated double bonds by which the resin is capable of reacting with a polymerizing mixture of acrylamide/N,N-methylenebisacrylamide used in producing polyacrylamide electrophoretic gels. As understood herein, "active hydrogens" are those hydrogen atoms in —OH, —SH, =NH, —COOH and —NH$_2$ functions. Film-forming resins derivatized as above described can be illustrated by, but not limited to, the following formula:

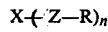

wherein Z stands for —O—, —S—, —N—, —(CO)N—, —(CO)S— and —(CO)O; X represents the residue of the hydrophilic, film-forming resin and R is an ethylenically unsaturated radical, typically containing 2 to 12 carbon atoms while n represents the degree of derivatization or substitution. In theory, derivatization can be 100% provided all of the hydrogens are replaced. Generally, derivatization will be adjusted to provide the degree of polarity needed to match that of the electrophoretic gel to promote optimum adhesion thereof to the resin layer. A low degree of derivatization leaves many free active hydrogens, thus affording a resin layer having predominately hydrophilic character; a high degree of derivatization, depending on the type and molecular dimension of the substituent, affords a resin layer that is predominantly hydrophobic. By thus controlling the polar properties of the resin as above indicated, electrophoretic supports of the invention can be fabricated, utilizing both physical and chemical bonding, to provide effective adhesion for a wide variety of electrophoretic gels. Preferably, the ethylenic unsaturation is introduced by way of an ether linkage—where Z is O and R is hydrocarbon in the formula—since ether bonds are resistant to hydrolytic cleavage and not likely to break down under conditions commonly encountered in carrying out electrophoretic processes. Ethylenic unsaturation can also be introduced by means of amide and ester functions but the resulting derivatized resin may be more prone to hydrolysis than an etherified resin. The hydrolysis of esterified resins can generally be held to acceptable levels by such expedients as selecting less reactive and/or sterically hindered structures. However, it appears that the herein modified resin, even those having a reactive unsaturated ester grouping such as a methacrylate, are intrinsically more resistant to moisture than the low molecular weight silane methacrylates of Radola.

Hydrophilic resins amenable to derivatization as above described embrace a wide variety of film-forming polymers including both synthetic and natural types. Thus, the hydroxyl groups of polysaccharides can react with such compounds as alkenylhalides, unsaturated aliphatic acylhalides, or oxiranes having reactive acryl-, allyl-, methacryl-, groups of the like. Polysaccharides derivatized in this manner make suitable coating polymers. Such polysaccharides may include agarose, dextran, chitosan, carrageenan, algin, furcellaran, laminaran, locust bean gum, guar gum, methyl cellulose, hydroxypropylcellulose, sodium carboxymethylcellulose, and the like. It may be necessary to insolubilize some of the water-soluble films by cross-linking the hydroxyl or carboxyl groups with a polyfunctional resin, such as a polyamide, melamine-formaldehyde, or dimethylol urea. Synthetic polymers can include polyvinyl alcohols, polyvinyl pyrrolidines, polyamines, polyacrylamides, and polyacrylic acids which can be easily derivatized with the functional groups described above and subsequently react with polymerizing acrylamide. In general, the derivatized hydrophilic resins used in coating the herein electrophoretic supports will have a molecular weight in a range of about 5000 to $5 \times 10^6$ daltons.

As above pointed out, the herein film-forming hydrophilic resins are prepared by replacing active hydrogens in known hydrophilic resins with ethylenically unsaturated groups to provide derivatized resins such as those exemplified in the formula. This is effected following published synthetic procedures such as the preparation of modified agarose and agar described in U.S. Pat. No. 3,956,273 to Guiseley. According to this patent, the OH groups in the hydrophilic resins agarose and agar are reacted with acyl and alkylating reagents including ethylenically unsaturated members to provide a variety of resin derivatives. In carrying out these reactions the resin is first dissolved in strong aqueous alkali, about 0.5 to 1.5 molar in alkali metal hydroxide, after which the ethylenically unsaturated etherification or acylating reagent is added. Examples of etherification agents include alkenyl halides, for example, 3-bromopropene, 3-bromo-2-butene, 4-bromo-2-hexane, etc.; also allylglycidyl ether; acylating agents include acryloyl chloride, chloride, crotonyl chloride, methacryloyl chloride, etc. Since some discoloration or darkening of the solution tends to occur during the reaction when it is carried out in aqueous alkaline solution, producing a product which is discolored although otherwise entirely satisfactory, it is also preferred to block the aldehyde end group of the agarose, for example by reduction, before bringing the agar or agarose into contact with aqueous alkali, thus preventing the color-forming reaction which involved the aldehyde group from taking place. The blocking agent of choice is a borohydride, particularly an alkali metal borohydride such as sodium borohydride, which reduces the aldehyde end group to an alcohol (hydroxy) group.

The reaction is preferably carried out at an elevated temperature from about 70° C. to 100° C. or more, but lower temperatures may be used to minimize discoloration if the aldehyde end group is not blocked or to reduce loss when a relatively volatile reagent is used. At lower temperatures the reaction is slower and in some cases the selected reagent is decomposed by reaction with the water before the desired extent of reaction with agarose can be achieved.

After completion of the reaction, the mixture is cooled to 50° C.–60° C. (if it is at a higher temperature), the alkali is neutralized with an acid or is removed by dialysis or other conventional procedure, and the product is purified by conventional procedures. For example, the solution may be gelled by cooling, frozen and allowed to thaw, then washed and dried, or the product may be precipitated from the reaction solution by mixing with a water-miscible organic liquid which is a non-solvent for the product, such as methanol, ethanol, propanol, acetone, etc. after which the precipitate is filtered, washed with the non-solvent and dried.

These preparations can also be carried out in an organic solvent such as N,N-dimethylformamide, pyridine, or the like, particularly for acylation. Under these conditions, blocking of the aldehyde end group is usually unnecessary, little or no discoloration occurring during the reaction. In addition, acid anhydrides can be employed for acylation instead of acyl halides if desired.

The precise amount of alkenylating or acylating agent employed depends upon the conditions of the reaction and the extent of substitution (D.S.) desired. Usually a large excess above the amount theoretically necessary is used because of the tendency of the agent to react to some extent with water, when present.

The surface of the organoplastic film base can be rendered hydrophilic following any number of procedures familiar to the art. For instance, a hydrophilic surface can be formed on plastic film by treatment thereof with concentrated sulfuric acid; U.S. Pat. No. 3,960,499 to White. Apparently, sulfate radicals become superficially attached to the plastic film thereby clothing it in a hydrophilic skin. Another technique of providing a hydrophilic surface on the film base is to coat it with epoxy compounds; U.S. Pat. No. 4,072,639 to Yamaguchi et al. A still further example is treatment of the film base with alkali as described in the aforecited Radola publication. In one preferred procedure, the hydrophilic surface is formed by subjecting the plastic film to a corona discharge in the presence of oxygen; U.S. Pat. No. 3,549,406 to Ambusk. The hydrophilic character is created as a result of the oxygen being taken up at residual carbon-carbon double bonds in the plastic to form an oxirane structure. A still further method of effecting adhesion of the derivatized polyol to the film base is to incorporate a soap or surfactant in the coating composition. In this approach no special treatment of the film surface is necessary. It is believed that some of the surfactant molecules are oriented in such a manner that their hydrophobic moieties become affiliated with the hydrophobic film surface while the hydrophilic moiety is disposed outwardly. The resulting hydrophilic surface exerts an affinity for the hydrophilic derivatized resin thereby promoting bonding to the plastic film base. For purposes herein, this procedure is considered to fall under or to be equivalent to the herein definition of rendering the surface of the plastic film hydrophilic.

Reference is now made to the following non-limiting examples:

SYNTHESIS OF DERIVATIZED POLYOLS

Example 1

Allylglycidylagarose

Agarose (10 grams) is dissolved in 490 ml of boiling water. The solution is maintained at 80° C. and 10 ml of 4.4 M sodium borohydride in 14 M sodium hydroxide is added with constant stirring. After ten minutes, 100 ml of a 10% sodium hydroxide solution is added, followed by the drop-wise addition of 25 ml of allylglycidyl ether over a 15-minute period. After one hour, an additional 25 ml of allylglycidyl ether is added as before and reacted for another hour. The reaction mixture is cooled to 60° C. and then neutralized by the addition of 4 M acetic acid as indicated by phenolphthalein. The solution is slowly added to 3 volumes of isopropanol, yielding a white precipitate, which is recovered by filtering through a dacron cloth. After two washings in 2 liters of 60% isopropanol, the precipitate is oven dried overnight at 60° C. and ground to a fine powder. The derivatized agarose had its initial gelling temperature (42° C.) lowered to 16° C.

Example 2

Allylglycidyldextran

Fifty grams of dextran (MW ~250,000) is dissolved in 500 ml of water and heated to 80° C. in a constant water bath. The solution is maintained at 80° C. and 15 ml of 4.4 M sodium borohydride in 14 M sodium hydroxide is added with constant stirring. After 10 minutes, 100 ml of a 25% sodium hydroxide solution is added, followed by the drop-wise addition of 50 ml of allylglycidyl ether over a 30 minute period. After two hours, an additional 25 ml of allylglycidyl ether is added and the reaction allowed to continue for another two hours. The reaction mixture is cooled to 60° C., and then neutralized by the addition of 4 M acetic as indicated by phenolphthalein. The solution is slowly added to 3 volumes of isopropanol, yielding a white gelatinous precipitate. This is cooled down to 0° C. and the alcohol decanted off. The solidified precipitate was redissolved in 500 ml of water at 60° C. and again added to 3 volumes of IPA and cooled to 0° C. The solidified precipitate was recovered after decanting and oven dried overnight at 60° C. and ground to a fine powder.

PREPARATION OF ELECTROPHORETIC SUPPORTS

Example 3

Coating Polyester Film with Allylglycidylagarose

A sheet of polyester film (110 mm×125 mm) was placed in a plasma chamber (Model #2005 T-1818 SCA, made by Dionex of Sunnyvale, Calif.) and subjected to the following conditions:

Gas: Oxygen
Pressure: 0.5 Torr
Power: 100 Watts
Time: 5 Minutes

Following plasma treatment, the film was dipped in an 0.5 aqueous solution of the allyglycidylagarose of Example 1. The coated film was then dried in an oven at 100° C. for 20 minutes.

Example 4

A sheet of polyester film (110 mm×125 mm) was dipped in an 0.5% solution of allylglycidylagarose in 0.1% Triton X-100, available from the Rohm & Haas Co., Philadelphia, Pa. The wetted film was then heated in an oven at 110° C. for 20 minutes.

Example 5

Polyacrylamide Gel Electrophoresis on Allylglycidylagarose Coated Polyester Film Sodium dodecylsulfate polyacrylamide electrophoresis was performed using the method described by U. K. Laemmli (Nature 227, 680, (1970)). In this procedure the casting apparatus for forming the polyacrylamide gel consists of a rectangular glass plate (15.9 cm×14 cm) and a notched glass plate supplied by Aquebogue Machine and Repair Shop (Aquebogue, L.I., N.Y.). The coated plastic was placed on top of the rectangular glass plate with the hydrophilic side containing the allylglycidylagarose film facing outwards. Three plastic spacers 1.2 mm thick were placed in a U-shape configuration over the edges of the glass-supported plastic and the notched glass plate placed on the spacers and held in place with six spring clamps. The resulting casting chamber was supported in a vertical position and 30 ml of a 0.375 M Tris-HCl (pH 8.8) solution containing 12% acrylamide, 2.6% N,N'-methylenebisacrylamide, 0.1% sodium dodecylsulfate, 0.025% tetramethylethylenediamine and ammonium persulphate was added. Following polymerization, which results in a gel being formed, a stacking gel is prepared by layering on top of the previous gel 10 ml of a 0.125 M Tris-HCl (pH 6.8) solution containing 3% acrylamide, 2.6% N,N'-methylenebisacrylamide, 0.1% sodium dodecylsulfate, 0.025% tetramethylethylenediamine and ammonium persulfate. Sample slots are formed using a teflon comb and following polymerization of the stacking gel, the glass cassette is placed into an electrophoretic chamber manufactured by Aquebogue Machine and Repair Shop where protein samples ranging in molecular weight from 17,000 to 200,000 daltons were prepared at a concentration of 10 mg/ml in 0.0625 M tris(hydroxymethyl)aminomethane-HCl (pH 6.8) containing 2% sodium dodecylsulfate, 10% glycerol, 5% 2-mercaptoethanol and 0.001% bromophenol blue and 5 l aliquots were added to the sample wells. The upper and lower reservoirs contained 0.025 M Tris, 0.192 M glycine and 0.1% sodium dodecylsulfate (pH 8.3). Electrophoresis was carried out at 25 m.a. for 2.5 hours. The polyacrylamide gel was removed from between the glass plates and found to be firmly attached to the plastic support. It was placed in a staining solution consisting of 0.05% Coomassie brillant blue R in 25% isopropanol, 10% acetic acid. Following overnight staining, the gel was destained for 4 hours in a solution of 45% methanol, 45% acetic acid. After this time, the protein bonds were visible and the gel could not be removed from the plastic support.

Example 6

Polyacrylamide pH Isoelectric Focusing on Allylglycidylagarose Coated Plastic

An ultra thin layer polyacrylamide isoelectric focusing gel was cast on the allylglycidylagarose coated plastic surface of Example 1. The gel-forming solution contained 5% acrylamide, 3% N,N'-methylenebisacrylamide, 10% glycerol, 2.5% Pharmalytes-pH 3–10 (Pharmacia Fine Chemicals, Piscataway, N.J.), and 0.07% ammonium persulfate. After casting the gel by the method described by B. J. Radola (Electrophoresis Vol. I, P. 43 (1980)) in which the gel is placed on the cooling platen of a flat-bed electrophoresis chamber (BioRad, Richmond, CA) and 5 μl of a protein sample was applied to the gel. The anolyte wick was soaked with 1 M $H_3PO_4$ and the catholyte wick contained 1 M NaOH. The sample was focused for 2 hours at a 1200 volt limit, at a 10 m.a. current limit, and at a 5 watt power limit. The gel was fixed in a solution containing 12% trichloroacetic acid and 3.4% salicylic acid for 30 minutes, then washed in 2 liters of $H_2O$ for 1 hour and finally stained and detained in Coomassie brillant blue R250 as described in Example 5. Throughout the entire procedure the gel remained firmly attached to the treated plastic support.

In the examples aforesaid, Tris-HCl is tris(hydroxymethyl)aminomethane-HCl.

What is claimed is:

1. A support for an electrophoretic medium comprising a base plate of an organoplastic sheet film and an adherent resin coating applied to at least one side of said base plate, said resin coating containing ethylenically unsaturated groups capable of undergoing copolymerization with acrylamide.

2. The support according to claim 1 wherein the organo plastic sheet film is selected from the class consisting essentially of polystyrene, polypropylene, styrene-acrylonitrile copolymer, polycarbonate, cellulose acetate propionate, cellulose acetate, butyrate, nitrile-acrylonitrile-styrene terpolymer, polyacrylate, polymethacrylate, polyterephthalate and acrylonitrile-butadiene-styrene copolymer.

3. The support of claim 1 wherein the ethylenically unsaturated groups in the resin consist of ethylenically unsaturated hydrocarbon radicals of 2 to 12 carbon atoms connected to said resin through functional linkages selected from the class consisting of —O—, —S—, —N—, —O(CO)—, S(CO)— and —(CO)N— linkages.

4. The support according to claim 1 wherein the resin coating is in the form of a separately applied film-forming adherent coating.

5. The support according to claim 4 wherein the coated side of the base plate and the resin coating are hydrophilic.

6. The support according to claim 5 wherein the hydrophilic surface on the coated side of the organoplastic sheet film is formed by contacting it with an electric discharge.

7. The support according to claim 3 wherein the resin is a polysaccharide.

8. The support according to claim 7 wherein the polysaccharide is agarose.

9. An electrophoretic support comprising a base plate of an organoplastic film sheet one side of which has been rendered hydrophilic by contact with a plasma chamber and having applied to said hydrophilic side a coating of allylglycidylagarose.

10. The support according to claim 9 wherein the organoplastic film is polyester film.

11. An electrophoretic element, for use in electrophoretic separations, comprising the support of claim 1 coated with electrophoretic medium.

12. The electrophoretic element of claim 11 wherein the electrophoretic medium is selected from the class consisting of polyacrylamide and agarose gel films.

13. An electrophoretic element, comprising the support of claim 9 coated with an electrophoretic medium.

14. The electrophoretic element of claim 13 wherein the electrophoretic medium is selected from the class consisting of polyacrylamide and agarose gel films.

15. The electrophoretic element of claim 14 wherein the electrophoretic medium is a polyacrylamide gel film.

16. The electrophoretic element of claim 14 wherein the electrophoretic medium is an agarose gel film.

* * * * *